United States Patent [19]

Haynes

[11] Patent Number: 5,482,466
[45] Date of Patent: Jan. 9, 1996

[54] FLOSSING TOOL

[76] Inventor: Patrick M. Haynes, P.O. Box 532, Penryn, Calif. 95663

[21] Appl. No.: 89,699

[22] Filed: Jul. 9, 1993

[51] Int. Cl.[6] ................................................. A61C 15/00
[52] U.S. Cl. ........................................... 132/323; 132/324
[58] Field of Search ..................................... 132/323, 324, 132/325, 328

[56] References Cited

U.S. PATENT DOCUMENTS

| | | | |
|---|---|---|---|
| 1,644,390 | 10/1927 | Miller | 132/323 |
| 3,533,420 | 10/1970 | Maloney et al. | 132/325 |
| 3,642,011 | 2/1972 | Thompson | 132/323 |
| 3,896,824 | 7/1975 | Thornton | 132/89 |
| 4,030,199 | 6/1977 | Russell | 32/40 R |
| 4,133,339 | 1/1979 | Naslund | 132/89 |
| 4,178,947 | 12/1979 | McCourry et al. | 132/324 |
| 4,222,143 | 9/1980 | Tarrson et al. | 15/105 |
| 4,597,398 | 7/1986 | Chu | 132/92 R |
| 4,671,307 | 6/1987 | Curbow et al. | 132/323 |
| 4,691,404 | 9/1987 | Tarrson et al. | 15/167 R |
| 4,920,993 | 5/1990 | Mackie | 132/324 |
| 4,936,326 | 6/1990 | Eckroat | 132/326 |
| 4,982,752 | 1/1991 | Rodriguez | 132/327 |
| 5,101,843 | 4/1992 | Peng | 132/323 |
| 5,123,432 | 6/1992 | Wyss | 132/323 |
| 5,125,424 | 6/1992 | Eisen | 132/323 |
| 5,139,038 | 8/1992 | El Gazayerli | 132/325 |
| 5,141,008 | 8/1992 | Lee | 132/325 |
| 5,280,797 | 1/1994 | Fry | 132/323 |

Primary Examiner—Cary E. O'Connor
Attorney, Agent, or Firm—Bernhard Kreten

[57] ABSTRACT

A flossing instrument 10 that facilitates flossing and is utilizable by persons fitted with common orthodontic braces. The instrument 10 includes a combination floss spool cavity 22 and handle 20 to which is connected an arm 50 with two floss supports 100, 140 traversely mounted at a distal end 54 of the arm 50 remote from the handle. One support forms a tower 100 which is replaceable and interchangeable with a multitude of possible supports of differing functional applications. The tower 100 fits in the limited space between an orthodontic arch-wire W and the adjacent teeth T to be flossed. The instrument 10 includes a means to tension the floss F, a means to advance the floss F across the supports 100, 140, and results in a floss F action that uniquely moves through the adjacent teeth T at an angle while continually advancing new floss F'. Use of this instrument 10 provides a flossing process that is gentler and more controlled because the instrument 10 remains stationary when the floss F overcomes the tightest spacings between adjacent teeth T. The instrument 10 accomplishes flossing while both hands can remain comfortably outside of the mouth.

27 Claims, 5 Drawing Sheets

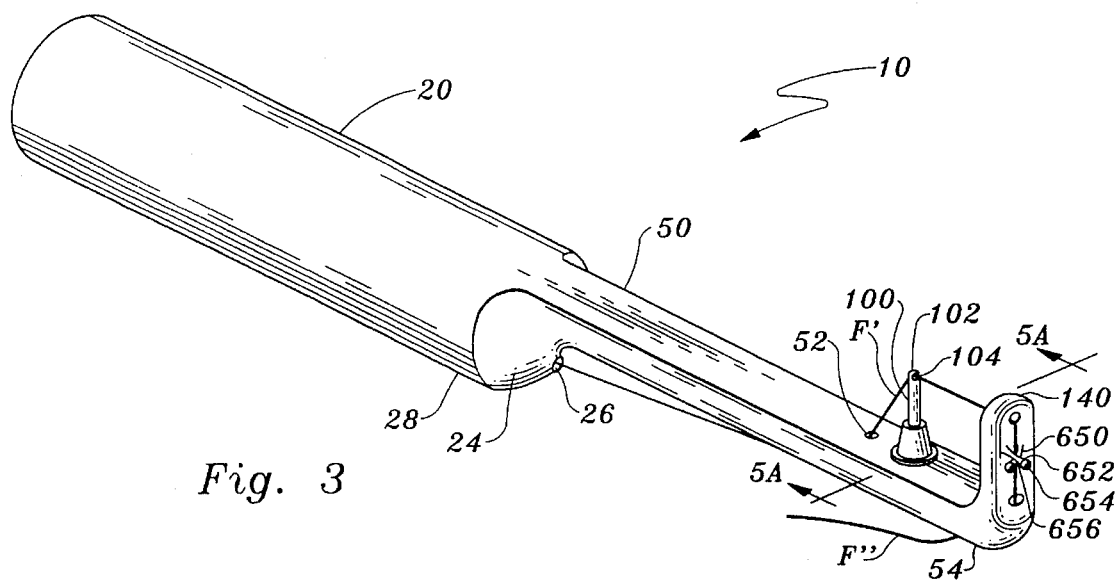
Fig. 3
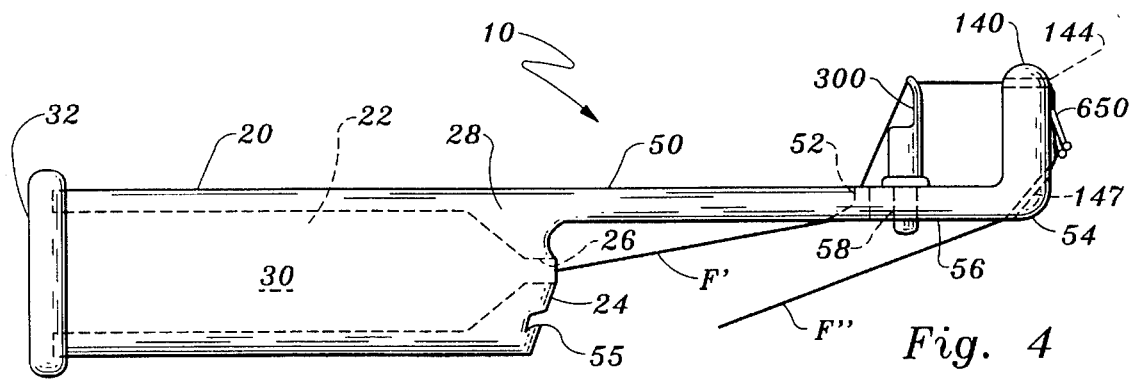
Fig. 4
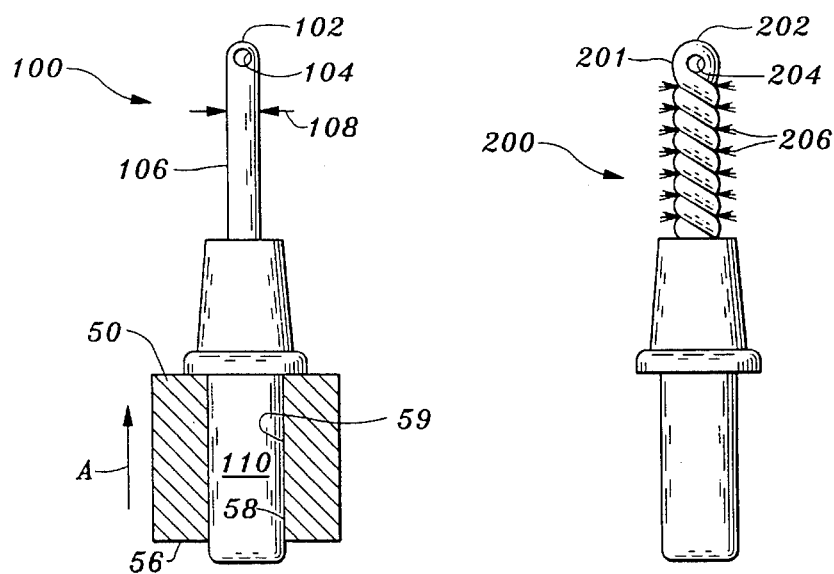
Fig. 5A
Fig. 5B

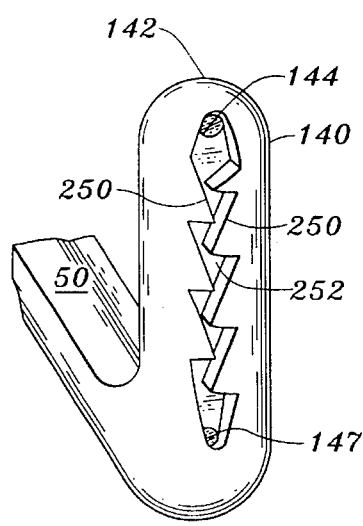
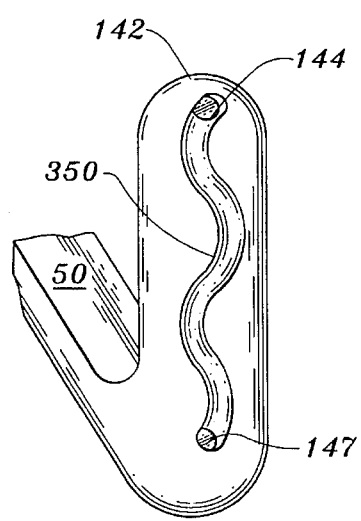
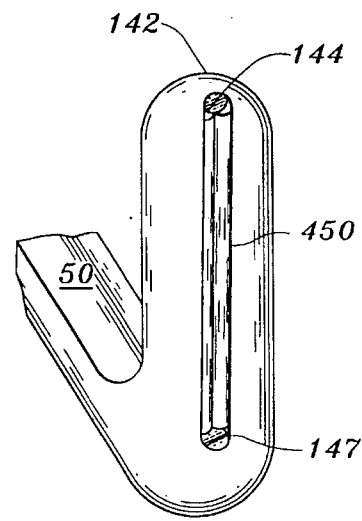
Fig. 6A      Fig. 6B      Fig. 6C
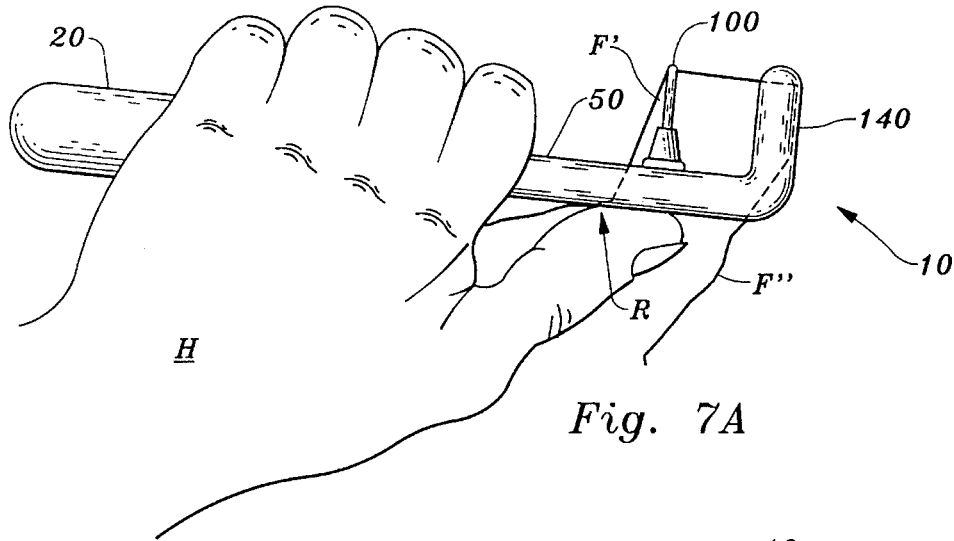
Fig. 7A
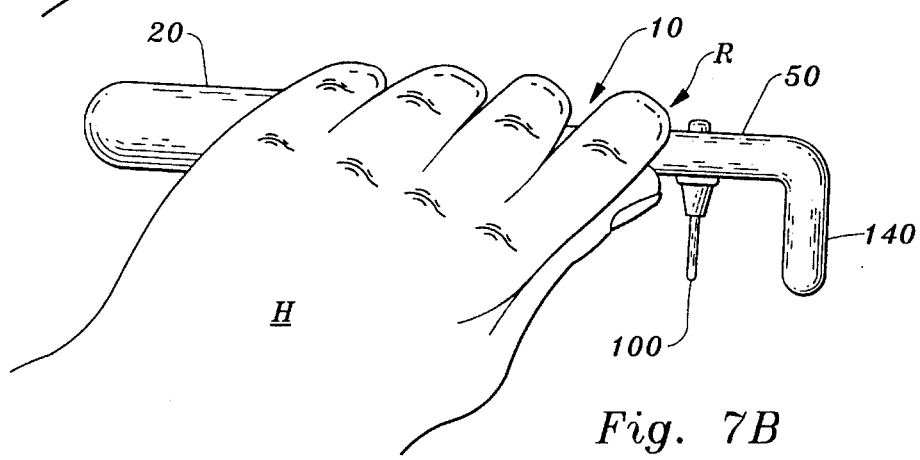
Fig. 7B

FLOSSING TOOL

FIELD OF THE INVENTION

This invention relates to instruments for assisting a person in flossing their teeth by supporting the floss. More particularly, this invention relates to floss supporting instruments which can direct floss into an interproximal space between teeth of a person who wears orthodontic braces including an arch-wire.

BACKGROUND OF THE INVENTION

While only 4 percent of Americans believe that they have gum disease, the reality is that 75 percent actually do. This number is nearly directly proportional to that percentage of Americans who do not floss on a regular basis, if at all. And in a country where it is widely recognized that prevention is the best medicine, there is obviously plenty of room for improvement. So with the number of people with gum disease being what it is, and flossing being the best means of prevention, it is not surprising that, although both are useful, flossing is recognized as being more important to oral hygiene and health than brushing teeth.

Although many flossing instruments have been designed (as is apparent by the number of patents issued in this field and listed below), few go to market. About the only flossing instruments available are the "forked wand-like" floss holders such as those taught by Lee in U.S. Pat. No. 5,141,008, Eisen in U.S. Pat. No. 5,125,424, and El Gazayedi in U.S. Pat. No. 5,139,038. These devices have a serious drawback in that the user typically winds the floss around pegs in order to fix the floss between the supports. Thus, when the floss between the supports is spent or severed between the tight spacings of adjacent teeth, the user must unwind, advance, and then rewind the floss before proceeding. This is very time consuming and usually leaves the user sticking to the common method of winding the floss around their fingers (which has its own drawbacks: hurts the fingers and is awkward).

Although there are many inventions where the floss is more easily dispensed and advanced across the floss supports, many are not only too complicated to use, but also too complicated to manufacture for a price which would encourage the public to try them, and some just simply do not work effectively. The prior art that would possibly result in a useful instrument typically is made of several pieces that require a great deal of pre-marketing assembly which in turn increases the price. "Forked wand-like" floss holders have both the manufacturing and market price advantage in that they are made in a single molding process, but still as aforementioned, their usefulness is quite limited.

Another situation, other than the lack of a good flossing instruments, that causes people to neglect flossing is when they are fitted with orthodontic braces. The fact that most of those fitted with braces are children who are less likely to see the long-term benefits of flossing only makes things worse. With this being the case, and many children gaining bad habits that will be hard to change (which is apparent from the large percentage of adults that floss very little, if at all) there is quite a bit of room here, regardless of the number of prior art patents, for improvement.

The most common current method of flossing with braces requires the threading of the floss behind the arch-wire that is fitted to all the brackets which are adhesively fixed to the fronts of the teeth. This process must be repeated for every gap between adjacent teeth and is extremely time consuming.

Accordingly, for persons having braces, a great need exists for an instrument that somehow works behind the arch-wire to eliminate the threading procedure and thus speed up the flossing operation. The problem arose: what is structurally stable while still being small enough to fit behind the orthodontic arch-wire (approximately 0.040 inches thick×0.080 inches wide). Commonly, most of the gaps between orthodontic arch-wire and the teeth are greater than 0.040 inches. However, in some cases there is little more than 0.040 inches.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| U.S. PAT. NO. | ISSUE DATE | INVENTOR |
|---|---|---|
| 3,896,824 | July 1975 | Thornton |
| 4,030,199 | June 1977 | Russell |
| 4,133,339 | January 1979 | Naslund |
| 4,222,143 | September 1980 | Tarrson |
| 4,597,398 | July 1986 | Chu |
| 4,691,401 | September 1987 | Tarrson |
| 4,920,993 | May 1990 | Mackie |
| 4,982,752 | January 1991 | Rodriguez |
| 5,101,843 | April 1992 | Peng |
| 5,123,432 | June 1992 | Wyss |
| 5,125,424 | June 1992 | Eisen |
| 5,139,038 | August 1992 | El Gazayerli |
| 5,141,008 | August 1992 | Lee |

U.S. Pat. No. 4,597,398, to Chu, teaches the use of a tool that goes behind the arch-wire and provides a post to be 0.5 mm (0.020 inches). This instrument requires the user to reach inside their mouth to force the floss between adjacent teeth whereas this invention has a second floss support that goes behind the teeth and allows the user to keep both hands outside one's mouth.

U.S. Pat. No. 4,920,993, to Mackie teaches a tool that allows the user to keep both hands outside the mouth, but uses two separate "pistol-looking" floss supports, one each held in separate hands. This would be quite difficult to coordinate because the instrument is basically an extension of each of the user's hands, not their own hands by themselves. By contrast, with the instant invention, the two floss supports are fixed relative to one another, and thus once the outer support is aligned, the inner support is inherently generally aligned. Mackie's invention is also unsanitary in that the unit would tend to collect food debris in his pick up apparatus that was recently dislodged from the teeth during the flossing process. It is also improbable that the complicated design of this invention would result in an instrument that is marketable due to its high manufacturing cost.

U.S. Pat. No. 5,101,843, to Peng is a disposable flosser, and thus quite expensive to use on a regular basis, unlike the present invention which is suitable for repeated use until the spool is spent. Even then, it is possible the spool could be replaced. In addition, serious doubts exist about the advantages, and perhaps some drawbacks, of the Peng curved floss supports. Injury to the gums is avoided with the first support of the present invention because the user gently inserts the first floss support behind the arch-wire while the floss is relaxed. The floss is then forced between adjacent teeth after the entire instrument, and thus support, is secured and stationary. The floss of Peng's invention is always taut. It is also possible that if the curved floss support of Peng's invention has been rotated around the arch-wire (per his described method) and then the floss becomes caught in the tight spacings between adjacent teeth, it would leave the user prone to catching the arch-wire with the curved floss support, when the floss comes free, with enough force to cause the user's teeth to ache, if not damage the braces. In the use of the present invention, if the floss becomes caught between adjacent teeth, the floss is simply relaxed, the support gently removed from behind the arch-wire, and then the floss is safely pulled free.

Many other patents, such as Nos. 5,125,424 and 5,141,008, provide two fixed floss supports, dispensing and floss advancing ability, but none are tailored for those fitted with braces. Also, none of the prior art has described the floss action of the present invention as the floss moves through adjacent teeth, nor has taught the automatic floss advancing means inherent to the instant instrument's method of use (to be detailed). Without this method of use, the users of the prior art are resigned to forcing a taut strand of floss between adjacent teeth by manipulating the entire instrument, via the handle, in a prying motion. With the instant instrument, the user simply pulls gently on the pick-up end of the floss (which is conveniently located outside the mouth) while the instrument remains stationary.

Also, in most other inventions (e.g. U.S. Pat. No. 5,125,424), the arm (the functional part that is inserted in the mouth) and the handle/floss spool cavity are separate pieces that plug together. It is doubtful whether this press fitting could be maintained while continually being stressed when repeatedly forcing the floss between the tightest spacings of adjacent teeth. Since the instrument of the present invention is stationary when the floss moves through the adjacent teeth, this would not be a drawback. Additionally, the floss spool access is located at the side of the handle opposite the arm to maintain a one mold manufacturing process. The cap is connected to the floss spool cavity via a plastic hinge; cap and hinge both being molded with the remainder of the instrument in one molding process. As a result, the other flossing instruments are more difficult to manufacture.

SUMMARY OF THE INVENTION

A flossing tool is provided which is configured to facilitate flossing of teeth having an arch-wire, such as that provided for various orthodontic procedures extending along the teeth and slightly spaced therefrom. The flossing tool includes a handle graspable by a user with an arm extending therefrom. The arm includes a tower (or first support) extending perpendicularly from a top surface thereof and a second support extending from a top surface thereof. The tower and second support are spaced a distance apart not less than a length of an interproximal space between adjacent teeth which are to be flossed.

The tower is dimensioned to have a thickness not greater than the depth of a space between the arch-wire and the interproximal space to be flossed Thus, the tower can fit into this interproximal space with the second support located adjacent to the interproximal space, but on the side of the interproximal space opposite from the tower.

Both the tower and the second support include apertures at distal ends thereof which slideably support the floss therethrough. Thus, when the tower is located between the arch-wire and one side of the interproximal space and the second support is located on a second side of the interproximal space, the floss is located within the interproximal space for flossing therewithin.

Once this interproximal space has been flossed, the flossing tool is removed from the interproximal space along with the floss. The floss is then advanced automatically when the tower is inserted in the next interproximal space, allowing a clean portion of the floss to be utilized in this new interproximal space. In this way, clean floss is presented for flossing of each interproximal space. A floss advancement means is thus inherent in this invention's method of use.

The flossing tool preferably includes a cavity within the handle which receives a spool of floss therein. Also, the second support preferably includes a unidirectional floss movement means which prevents the used floss from backing up into a region between the tower and the second support after its use. This unidirectional floss movement means also facilitates handling the floss with only a single hand of the user.

The tower is preferably removable so that it can be replaced when damaged or when other specialized tools, such as a dual purpose wire filament floss support are to be used. An arm aperture preferably allows the floss to pass from a bottom side of the arm through to a top side of the arm near the tower so that a thumb or index finger of the user can easily trap against the arm an unused end of the floss distant from the second support. In this way, the unidirectional floss movement means holds one end of the floss, with aid from the opposite hand, and the thumb or index finger holds the other end of the floss so that the floss remains taut between the tower and the second support while scraping the teeth near the gum line.

OBJECTS OF THE INVENTION

Accordingly, it is a primary object of the present invention to provide a flossing tool which directs floss into interproximal spaces which are bounded by an arch-wire.

Another further object of the present invention is to provide a flossing tool which can be utilized by people with braces which include arch-wires by manipulating the tool with only a single hand holding the floss.

Another further object of the present invention is to provide a flossing tool with fresh floss for the flossing of each interproximal space.

Another further object of the present invention is to provide a flossing tool which does not require a user to place his hands within his mouth.

Another further object of the present invention is to provide a flossing tool which is gentle to the gums of the user.

Another further object of the present invention is to provide a flossing tool which utilizes floss sparingly and yet consistently provides fresh floss automatically for the cleaning of each interproximal space.

Another further object of the present invention is to provide a flossing tool which is easy to manufacture and lends itself to manufacture from low cost materials.

Another further object of the present invention is to provide a flossing tool which is easy to use and encourages a user to floss regularly.

Another further object of the present invention is to provide a flossing tool which simultaneously flosses interproximal spaces between teeth and also purges debris from a space formed between an arch-wire and the adjacent teeth.

Viewed from a first vantage point it is an object to provide a flossing instrument for locating and supporting floss in interproximal spaces between teeth of a user, the user having an arch-wire proximate to, yet spaced from the teeth and interproximal spaces, the flossing instrument comprising in combination a handle adapted to be grasped by a hand of the user, an arm extending away from the handle, a tower extending from a surface of the arm, the tower dimensioned with a thickness not greater than a distance between the arch-wire and the interproximal space, the tower including means for slideably supporting the floss, and a second support spaced from the tower, the second support including means for slideably supporting the floss, whereby floss can be inserted, utilized and removed from interproximal spaces blocked by the arch-wire.

Viewed from a second vantage point, it is an object to provide a method for flossing interproximal spaces between teeth which have an arch-wire proximate thereto, but spaced therefrom, the steps including providing a flossing tool having a tower dimensioned to fit between the arch-wire and the teeth of the user, the tower including a means to slideably support the floss thereon, and a second support with a means to slideably support the floss, the second support spaced from the tower a distance not less than a length of the interproximal spaces, supporting floss between the support means of the tower and the support means of the second support, locating the tower between the arch-wire and the interproximal space to be flossed, locating the second support on a side of the interproximal space opposite the tower, and utilizing the floss within the interproximal space.

These and other objects will be made manifest when considering the following detailed specification when taken in conjunction with the appended drawing figures.

BRIEF DESCRIPTION OF THE DRAWINGS

FIG. 3 is a perspective view of an alternate embodiment of this invention.

FIG. 4 is a side view in section of another alternative embodiment of this invention.

FIG. 5A is a sectional view taken along line 5A—5A of FIG. 3.

FIG. 5B is an alternative embodiment of the tower of this invention.

FIGS. 6A—6C are perspective views of various alternative embodiments of the floss anti-reversing means of this invention.

FIG. 7A and 7B are perspective views of the hand position while holding one embodiment of this invention.

DESCRIPTION OF PREFERRED EMBODIMENTS

Figure 1:
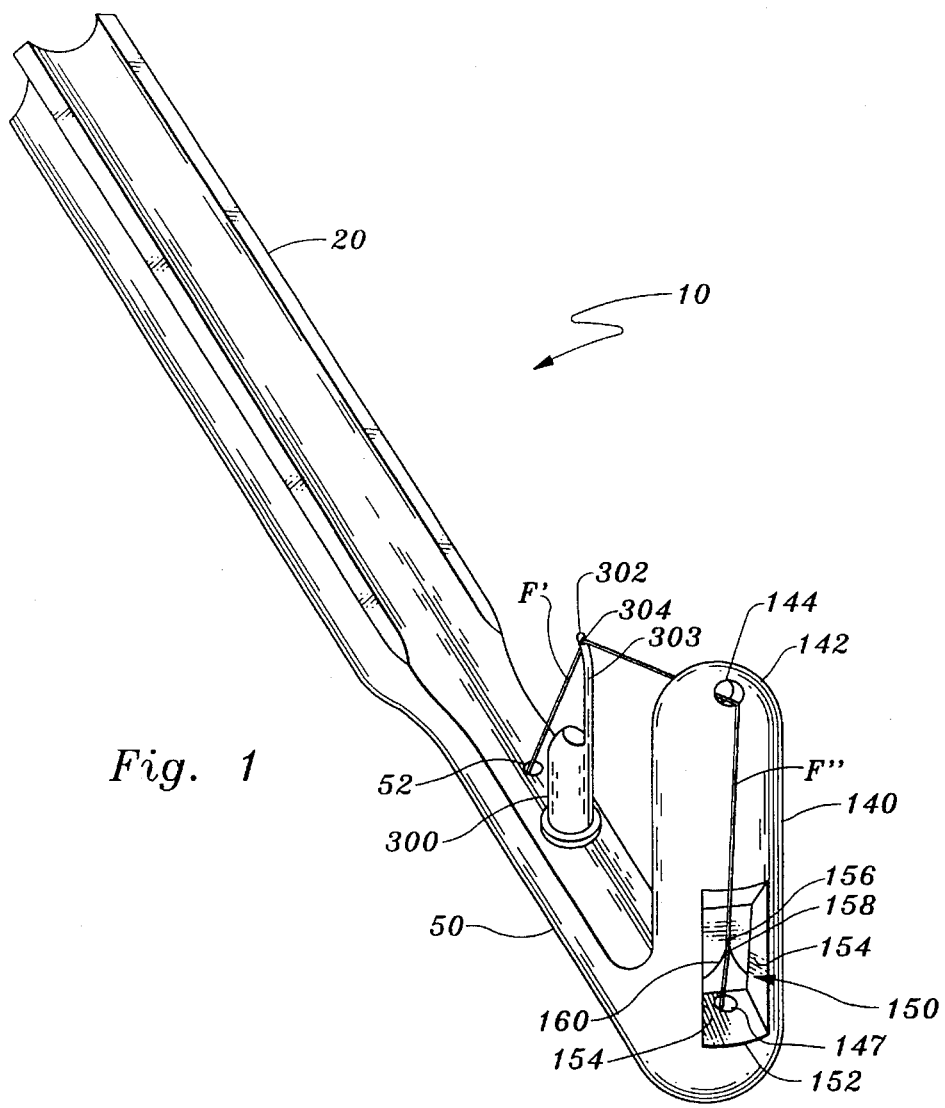
FIG. 1 is a perspective view of one embodiment of this invention.
Figure 2:
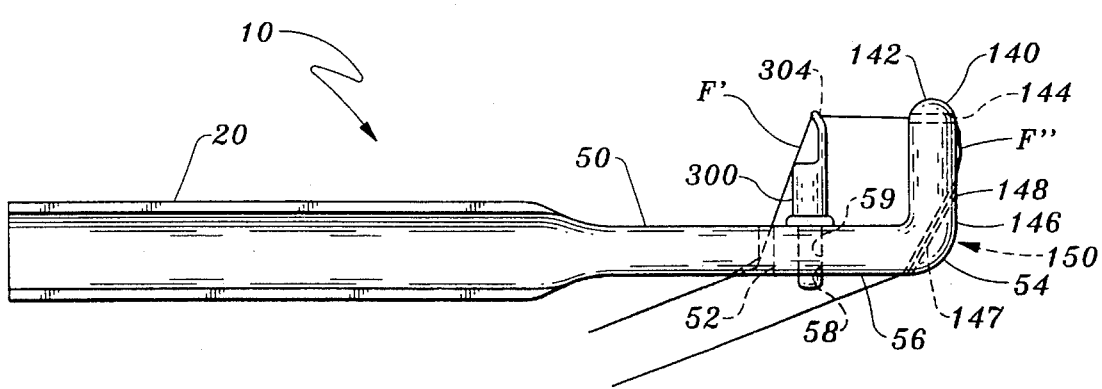
FIG. 2 is a side view in section of that which is depicted in FIG. 1.

Referring to FIGS. 1 and 2, a multi-situation flossing instrument 10 is shown which depicts an embodiment of this invention and includes: an elongate arm 50, a first floss support forming a tower 100 (FIG. 3), a second floss support 140, apertures 104,144 at distal ends 102,142 of the floss supports 100,140, respectively, through which a flossing material F is threaded, strung tautly, and advanced at any given time during the flossing operation. An aperture 52, which aligns the flossing material F adjacent to the first floss support 100, and an anti-reversing means 150, in the region subsequent in floss path to the aperture 144 of the second floss support 140, result in the one-way feeding of the flossing material F from the fresh floss F', or floss supply side of the flossing instrument 10. The first floss support tower 100 is replaceable by means including a frictionally retained press fitting 58 within a press fitting aperture 59 of the arm 50, and is interchangeable with a multitude of first floss support options (discussed below) wherein each of the possible first floss support options is specific for a given situation and/or flossing material.

Referring now to FIGS. 3 and 4, flossing instruments 10 are shown that depict alternate embodiments of this invention. The FIG. 3 embodiment exhibits features that differ from the first embodiment depicted in FIGS. 1 and 2 in that: a hollow handle 20 doubles as a cavity 22 for a floss spool 30, such to provide a continual floss F supply, and an aperture 26 is provided at the end of a conic shaped portion 24 at the arm end 28 of the handle 20, through which the flossing material F is threaded before continuing to the distal end 54 of the arm 50, which is identical to the distal end 54 of the embodiment of FIGS. 1 and 2. The FIG. 4 embodiment is distinctive in that a recessed shearing edge 55 is provided to cut the spent end of the flossing material F" at the end of each flossing operation. Also, both the FIG. 3 embodiment and the FIG. 4 embodiment exhibit an anti-reversing means 650 distinctive from that of FIGS. 1 and 2.

FIGS. 5A and 5B show end views of alternative embodiments of the replaceable first floss support 100 and 300 depicted in FIGS. 1-4. Common to all these views is a frictionally retained, press fitable insert portion 110 of the first floss support tower 100. FIG. 5A depicts in section the arm 50 surrounding the aperture 59 which the insert portion 110 fits tightly, and thus securely within. The insert portion 110 is of such dimension so as to extend through the press fitting 58 a suitable distance to aid in removing any first floss support 100 options, including those depicted in FIGS. 5A–5B, for replacement, by simply pressing from the bottom 56 of the arm 50 to initiate the removal, or backing out process along arrow A.

FIG. 5A shows the first floss support 100 depicted in the embodiment of FIGS. 3. It has a tower 100 with an aperture 104 adjacent but spaced slightly from the distal end 102 and passing through the tower 100 in a direction non-parallel to the tower 100. The distal end 102 is blunt and closed. This embodiment is suitable, but not exclusive, for use with common orthodontic braces, where the tower 100 must fit in the narrow space between the orthodontic arch-wire W and the teeth T being flossed. The dimensions of the tower 100 should preferably be 0.040 inches in depth 106, and 0.080 inches in width 108. This depth 106 and width 108 will allow the tower 100 to fit under the arch-wire W, but is of such dimension to maintain structural stability (if made of the proper material) and allows the aperture 104 to be of a suitable dimension for the threading of a floss F' strand through it. Any dimensions not greater than a distance between the arch-wire W and the teeth T can be utilized.

While the tower 100 is preferably straight, the tower can alternatively have a slight curve as exhibited in the tower 300 of FIGS. 1, 2 and 4. The tower 300 has a greater diameter base opposite a distal end 302. The distal end 302 has a bend 303, which can either be abrupt or gradual, and positions an aperture 304 further from the second support 140 than the base 306.

A suitable material for the tower 100 is Polyetherimide (PEI) which is currently manufactured by General Electric under the name ULTEM. ULTEM is available in FDA sanctioned grades that have proven quite effective in prototypes of this invention.

FIG. 5B depicts an alternate embodiment which is also useful for flossing in those cases where the user is fitted with orthodontic braces. This tower 200 consists of a twisted wire 201 with filaments 206, where the process of twisting the wire 201 is stopped short, or done in such a way (as with a small circular spacer at the top of the wire 201) so as to create an aperture 204 at the distal end 202 of the tower 200, through which a floss strand F' may be threaded.

This tower 200 results in a dual purpose cleaning operation where both the debris packed among the orthodontic braces and teeth T is cleared, and the flossing of the teeth T is accomplished. This speeds the flossing operation because it is quite common for those fitted with braces to floss their teeth T in two steps. First, the debris between the braces and teeth T must be purged by some means, one of which is a twisted wire filament device (small bottle-brush type instrument) before the second step of flossing the teeth T can be accomplished.

This is especially true when flossing with the common method currently used, threading the floss F behind the arch-wire W, because any obstruction, such as food debris that partially or entirely blocks the space behind the arch-wire W, makes the threading of a flimsy strand of floss F or fishing wire-like threader of floss F, difficult if not impossible until the debris is cleared. Also, it should be noted that the filaments 206 of this tower 200 will tend to float, or center the tower 200 in the space between the arch-wire W and the teeth T to be flossed.

Referring now to FIGS. 1, 2, and 6A through 6C, a series of views are shown that depict the embodiments of the anti-reversing means which is subsequent in the floss F" path to the aperture 144 of the second floss support 140. This anti-reversing means 150 results in the one-way feeding of the floss F from the floss supply side of the instrument 10. FIGS. 1 and 2 depict a preferred embodiment of the anti-reversing means 150. The anti-reversing means 150 is incorporated within the base aperture 147 and includes a rectangular recess 152 surrounding the aperture 147. The recess 152 includes two curving sidewalls 154 that converge to a point 156 at a first end 158 closest to the aperture 144. A second end 160 adjacent the aperture 147 is wider than the first end 158. The floss F slides between the two sidewalls 154 and is pinched at the point 156 if the floss F attempts to travel from the base aperture 147 toward the aperture 144.

FIG. 6A depicts an embodiment of the anti-reversing means 250 including a narrow recessed groove 252 with opposing, but staggered "saw-tooth-like" notches 250 which, when the floss F" is threaded therethrough, result in a resistance to the floss F" reversing its direction, but allows the user to conveniently advance the floss F" when necessary during the flossing procedure. Note the aperture 147 which enters at the base 146 of the second floss support 140 and exits diagonally at the distal end 54 of the bottom 56 of the arm 50. This base aperture 147, along with the food debris that partially or entirely blocks the space behind the arch-wire W, makes the threading of a flimsy strand of floss F or fishing wire-like threader of floss F, difficult if not impossible until the debris is cleared. Also, it should be noted that the filaments 206 of this tower 200 will tend to float, or center the tower 200 in the space between the arch-wire W and the teeth T to be flossed.

Referring now to FIGS. 1, 2, and 6A through 6C, a series of views are shown that depict the embodiments of the anti-reversing means 150 which is subsequent in the floss F" path to the aperture 144 of the second floss support 140. This anti-reversing means 150 results in the one-way feeding of the floss F from the floss supply side of the instrument 10. FIGS. 1 and 2 depict a preferred embodiment of the anti-reversing means 150. The anti-reversing means 150 is incorporated within the base aperture 147 and includes a rectangular recess 152 surrounding the aperture 147. The recess 152 includes two curving sidewalls 154 that converge to a point 156 at a first end 158 closest to the aperture 144. A second end 160 adjacent the aperture 147 is wider than the first end 158. The floss F slides between the two sidewalls 154 and is pinched at the point 156 if the floss F attempts to travel from the base aperture 147 toward the aperture 144.

FIG. 6A depicts an embodiment of the anti-reversing means 150 including a narrow recessed groove 252 with opposing, but staggered "saw-tooth-like" notches 250 which, when the floss F" is threaded therethrough, result in a resistance to the floss F" reversing its direction, but allows the user to conveniently advance the floss F" when necessary during the flossing procedure. Note the aperture 147 which enters at the base 146 of the second floss support 140 and exits diagonally at the distal end 54 of the bottom 56 of the arm 50. This base aperture 147, along with the aperture 144 at the distal end 142 of the second floss support 140, aligns the floss F" over the recessed groove 252 so that the user could simply (most likely with a fingernail) slip the floss F" over the notches 250 and into place in the recessed groove 252, where it would then tend to stay.

FIG. 6B depicts an alternate embodiment of the anti-reversing means 150 which is nearly identical to that embodiment depicted in FIG. 6A, with the exception of the shape of the notches 350. In this embodiment, the notches 350 have a curved edge instead of being pointed like saw teeth.

FIGS. 6C, 7A, 7B, and 8A through 8D are views of an alternative embodiment of the anti-reversing means 150 which includes a groove 450 extending from the aperture 144 to the aperture 147. The groove 450 includes a crease 452 at a bottom thereof tending to inhibit sliding of floss therein. While this groove 450 does not have a bias toward floss F motion away from the tower 100, it can be coupled with friction from the user's hand H to prevent the floss F from reversing.

FIGS. 3 and 4 depict another positive anti-reversing means including: two prongs 650 including knobs 654 at their distal ends 652, where the prongs 650 cross and maintain pressure between one another. Again, this can be accomplished during a single molding process by allowing the prongs 650 to be molded out of contact with one another, but at angles that cross. The prongs 650 would be of such dimensions so that they can then be flexed and overlapped, opposite to that position in which they were molded, creating a pressure at a crotch 656 where the prongs 650 cross.

The floss F" is simply threaded over the crotch 656 created by the prongs 650 and, subsequent to the aperture 144 at the distal end 142 of the second floss support 140, and prior to the aperture 147 that enters the back 148 of the base 146 of the second floss support 140 and exits on the bottom 56 of the distal end 54 of the arm 50. Note that the knobs 654 serve three purposes: avoids sharp edges, detour the prongs 650 from becoming uncrossed to their molded position (although they could simply be overlapped again), and detour the floss F" from coming out from between the prongs 650.

Note that the aforementioned anti-reversing means 150, 250,350,450,650 are inherent to a single molding process. However, other anti-reversing means, such as one-way wheels, spring loaded locking pins, slide locks, pawls, ratchets, etc., would also work.

Referring now to FIGS. 7A and 7B, a hand position is shown of the hand H which is holding any embodiment of this invention while flossing the upper and lower teeth T respectively. This is helpful in visualizing and fully understanding the invention's method of use description, discussed below with FIGS. 8A through 8D. Particularly important is the thumb position of FIG. 7A, and the index finger position of FIG. 7B. An appropriate finger traps the flossing material F' against the arm 50 in close proximity to the arm aperture 52 adjacent the first floss support tower 100.

Figure 8A:
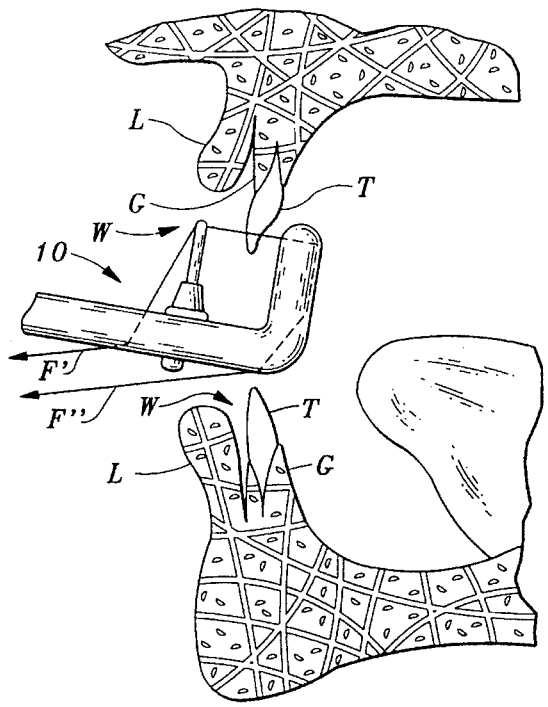
FIGS. 8A—8D are sectional views of the use method sequence of this invention and the floss advancement means that is inherent to the use method of this invention.

Referring now to FIGS. 8A–8D, the method sequence of this invention is depicted with the first floss support tower 100 of FIG. 3 (i.e. for a person fitted with common orthodontic braces). Also depicted in these figures is the floss advancing means which is inherent to the invention's method regardless of which embodiment is used. FIG. 8A shows the arm 50 of the instrument 10, positioned in the mouth with the tower 100 of the first support ready to be slipped behind the orthodontic arch-wire W. Also, notice the region R where the thumb, noted for clarity (or index finger when flossing lower teeth), would be located.

Figure 8B:
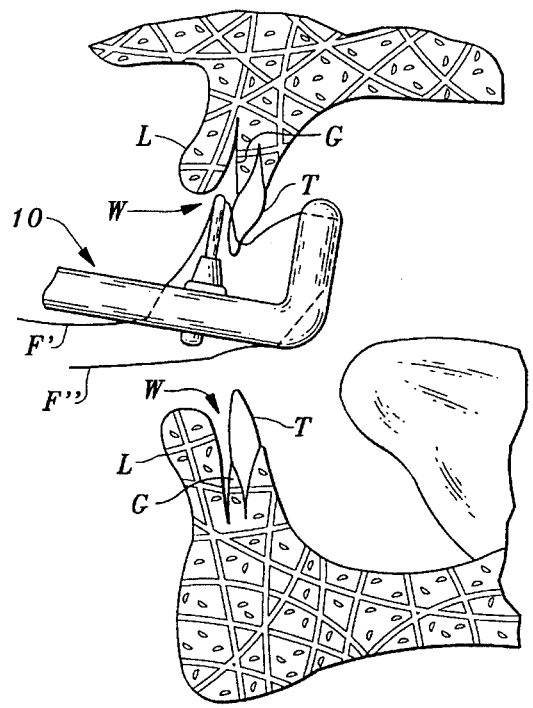

Still referring to FIG. 8A, with the thumb pinching the new floss F' against the arm, the floss F between the tower 100 region and the anti-reversing means 150 is taut. FIG. 8B shows the tower 100 once inserted behind the arch-wire W. During this insertion, the thumb is removed from contact with the arm 50, releasing the floss F'. Thus, when the tower 100 of the first support is inserted behind the arch-wire W, an amount of floss F (approximately ¼") is displaced, and thus fed from the floss supply side. Note that the anti-reversing means 150 need only be a resistance that is sufficient enough to cause the floss F to be displaced from the floss supply side during the insertion shown in FIG. 8B. This results in an automatic floss dispensing system inherent to the use of this, or any other embodiment of this invention.

Figure 8C:
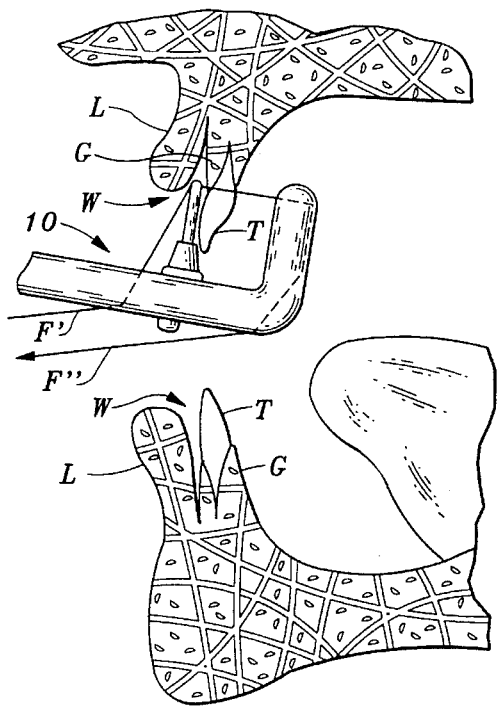

FIG. 8C shows the floss F between the teeth T being flossed. This has been initiated by replacing the thumb adjacent the arm 50, trapping the floss F thereto, and the off hand (or that hand not holding the instrument) pulling tight on the used floss F" from the floss pick-up side. With the floss F now in the gum area, the instrument 10 can be manipulated to scrape the surfaces of the teeth T being flossed.

Note that the insertion of the tower 100 has taken place while the floss F was in a relaxed position. Only when the tower 100 is resting against, and securely placed between the teeth T to be flossed, is the floss F tensioned. This has advantages over inserting a taut length of floss F between two adjacent teeth T of tight spacing. If the floss F is taut when inserting this, or any other instrument behind the arch-wire W, when the floss F overcomes the often tight spacings of the adjacent teeth T, the tower 100, or any other instrument of similar means, would be much more likely to gouge the gums G.

Also, with this instrument 10 stationary, and a single hand H in a much more controlled and convenient position (because it is comfortably situated outside the mouth) supplying a tensioning means while the floss F moves through the teeth T, there is less momentum carried into the gums G by means of the floss F (especially in the case of overcoming tight spacings). It will also be shown below, in the descriptions of FIGS. 9A–9D, that the floss F action of this invention results in a less resistant floss path through the tight spacings of adjacent teeth T, and thus reduces the chance of gouging the gums G by means of the floss F.

Figure 8D:
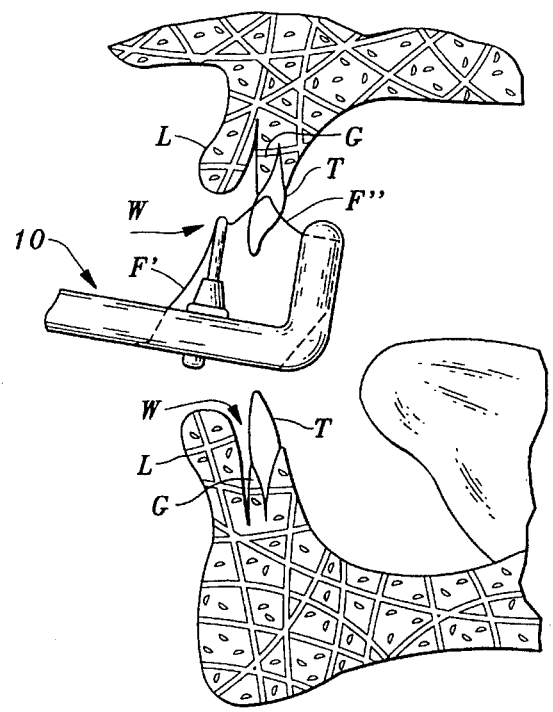

FIG. 8D shows the removal of the tower 100 from behind the arch-wire W. With the floss F still taut, the instrument 10 is simply removed. If there is any resistance to this, when it is overcome, the instrument 10 will simply slide out; Also, note that when flossing with the common method of threading the floss F behind the arch-wire W, it is difficult to do anything except abut against the arch-wire W when removing the floss F from between adjacent teeth T of tight spacing.

Although lengthy in description, after a few practice flossings to become familiar, repeating this procedure in all the gaps between adjacent teeth T results in flossing operation that is far easier, and less time consuming (approximately seven times faster than threading, for those fitted with braces). Note again, the floss advancement means inherent to the method of use for any embodiment of this invention. At approximately ¼ inch per gap, one flossing operation would be approximately 8 inches of floss F; less than half that suggested by a leading floss supplier in the instructional directions of their package.

Figure 9A:
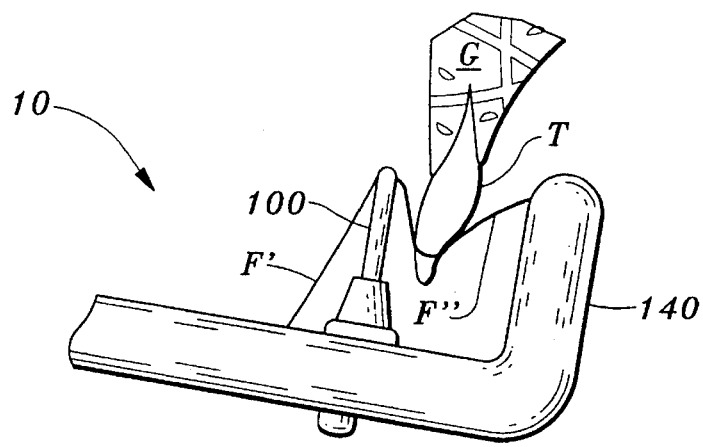
FIGS. 9A—9D are elevational views comparing-the floss action of this invention with that of other common flossing methods.
Figure 9C:
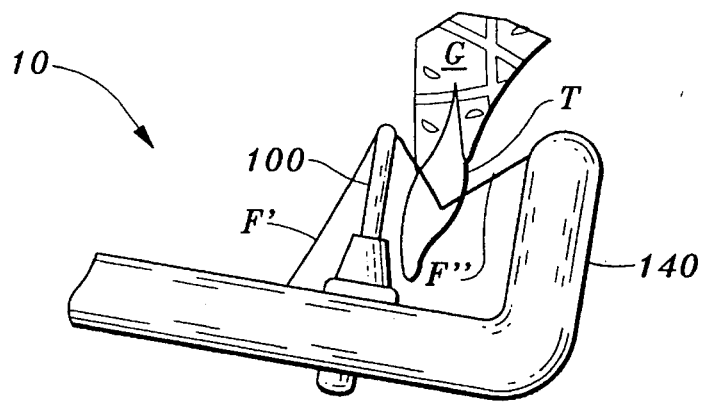
Figure 9B:
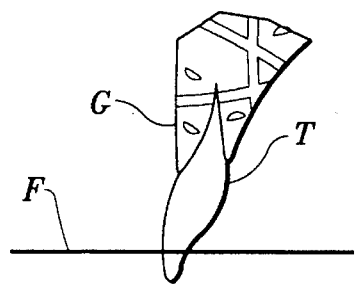

Referring now to FIGS. 9A–9D, a comparison is shown between the floss action of any embodiment of this invention, and that of the common flossing method, as the floss F moves through the gap adjacent the teeth T, and into the gums G. FIG. 9A shows the relative positioning of the floss F and the adjacent teeth T just after any tower 100 of this invention has been inserted into place, and prior to the floss F moving through the gap G of the adjacent teeth T. Notice the angle the floss F makes with respect to the teeth T when strung between the tower 100 and the teeth T. Also notice, that this length of the floss F is fresh due to the dispensing method aforementioned. Compare this with FIG. 9B and the right angle with which the floss F approaches the same teeth T when using the common flossing method. FIG. 9C shows the floss F of this invention moving through the tightest spacing region of the adjacent teeth T. Since the angle is maintained, the floss F tends to clear debris out of the gap of the adjacent teeth T, while continually rotating, and thus advancing the fresh portion of the floss F into the gap as the floss moves through the adjacent teeth T.

Figure 9D:
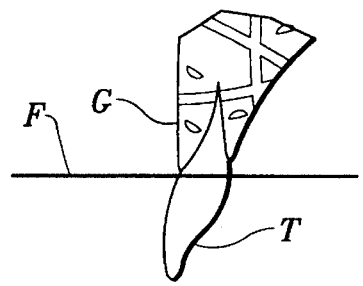

Compare this with the common flossing method depicted in FIG. 9D, and how the floss F would tend to pack debris into the gap, and eventually the gums G, of the adjacent teeth T. If the user tries to "saw" the floss F into the gap to clear debris and overcome the tight spacing, they repeatedly reintroduce used floss F into the gap, which often results in the shearing of the floss F between the tight spacings of the adjacent teeth T. Even if the user tries to advance the floss F only from the fresh floss side (which would be very difficult to coordinate with one hand in the mouth), it would be extremely difficult to accomplish this while only using ¼ inch of floss F.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A flossing instrument for locating and supporting floss in interproximal spaces between teeth of a user, the user having an arch-wire proximate to, yet spaced from the teeth and interproximal spaces, the flossing instrument comprising in combination:

a handle adapted to be grasped by a hand of the user, an arm formed with and extending away from said handle, a first support, configured as a tower and extending from a surface of said arm, said tower dimensioned with a thickness not greater than a distance between the arch-wire and the teeth of the user, said tower having a distal end spaced from said arm, said tower including means for slideably supporting the floss, said slideable support means oriented spaced from said distal end, and a second support extending from a surface of said arm and spaced from both said tower and said handle, said second support spaced from said tower by a distance not less than a length of the interproximal spaces, said second support closer to said tower than to said handle, said second support including means for slideably supporting the floss.

2. The flossing instrument of claim 1 wherein said second support includes a unidirectional floss translation means said unidirectional means including means to allow the floss to pass from said slideable support means of said tower toward said slideable support means of said second support, and means to prevent the floss from translating from said second support toward said tower.

3. The flossing instrument of claim 1 wherein said slideable support means of said tower is an aperture in said tower sized to allow the floss to pass therethrough, said aperture oriented non-parallel to a long axis of said tower.

4. The flossing instrument of claim 3 wherein said handle includes a cavity on an interior thereof supporting floss therein, said cavity including a conic shaped portion with an aperture sized to allow said floss to pass therethrough, the floss routed to exit said cavity aperture and then extend to said aperture in said tower.

5. The flossing instrument of claim 3 wherein said distal end of said tower is bent such that an extremity of said distal end is non-parallel with remaining portions of said tower.

6. The flossing instrument of claim 1 wherein said distal end of said tower is blunt.

7. The flossing instrument of claim 1 wherein said slideable support means is oriented to support the floss therethrough in an orientation non-parallel with a long axis of said tower.

8. The flossing instrument of claim 1 wherein said tower includes a continuous solid exterior surface.

9. The flossing instrument of claim 1 wherein said tower is solid.

10. A flossing instrument for locating and supporting floss in interproximal spaces between teeth of a user, the user having an arch-wire proximate to, yet spaced from the teeth and interproximal spaces, the flossing instrument comprising in combination:

a handle adapted to be grasped by a hand of the user, an arm formed with and extending away from said handle, a first support, configured as a tower and extending from a surface of said arm, said tower dimensioned with a thickness not greater than a distance between the arch-wire and the interproximal space, said tower including means for slidably supporting the floss, and a second support extending from a surface of said arm and spaced from both said tower and said handle, said second support spaced from said tower by a distance not less than a length of the interproximal spaces, said second support closer to said tower than to said handle, said second support including means for slideably supporting the floss;

whereby floss can be inserted, utilized and removed from interproximal spaces blocked by the arch-wire, wherein said second support includes a unidirectional floss translation means said unidirectional means allowing the floss to pass from said slideable support means of said tower toward said slideable support means of said second support, but preventing the floss from translating from said second support toward said tower, wherein said slideable support means of said tower is an aperture in said tower sized to allow the floss to pass therethrough, wherein said handle includes a cavity on an interior thereof supporting floss therein, said cavity including a conic shaped portion with an aperture sized to allow said floss to pass therethrough, the floss routed to exit said cavity aperture and then extend to said aperture in said tower, wherein said tower extends substantially perpendicularly from said arm, said tower including a proximal end connected to said arm and a distal end with an aperture.

11. The flossing instrument of claim 10 wherein an arm aperture is provided between said cavity aperture and said tower aperture, said arm aperture passing from a top surface of the arm which supports said tower thereon through to a bottom surface of the arm opposite the top surface;

whereby the floss can pass through the arm to a side of the arm opposite the tower where the floss can be conveniently trapped by the hand of a user, thereby preventing unneeded floss from exiting said cavity during the flossing operation.

12. A method for flossing interproximal spaces between teeth which have an arch-wire proximate thereto, but spaced therefrom, the steps including:

providing a flossing tool with a first support configured as a tower and dimensioned to fit between the arch-wire and the teeth of the user, the tower including a means to slideably support the floss thereon, and a second support with a means to slideably support the floss, the second support spaced from the tower a distance not less than a length of the interproximal spaces;

supporting floss between the support means of the tower and the support means of the second support;

locating the tower between the arch-wire and the interproximal space to be flossed;

locating the second support on a side of the interproximal space opposite the tower and in the interior of the mouth;

tensioning the floss between the tower and the second support while keeping the flossing tool stationary, such that the floss is caused to enter the interproximal space; and utilizing the floss within the interproximal space.

13. The method of claim 12 wherein said providing step includes the further step of configuring the second support to include a means to prevent translation of said floss away from said second support and toward said tower, whereby used floss having passed beyond said supporting means of said second support is prevented from backing up into a region between the second support and the tower.

14. A method for flossing interproximal spaces between teeth which have an arch-wire proximate thereto, but spaced therefrom, the steps including:

providing a flossing tool with a first support configured as a tower and dimensioned to fit between the arch-wire and the teeth of the user, the tower including a means to slideably support the floss thereon, and a second support with a means to slideably support the floss, the second support spaced from the tower a distance not less than a length of the interproximal spaces;

supporting floss between the support means of the tower and the support means of the second support;

locating the tower between the arch-wire and the interproximal space to be flossed;

locating the second support on a side of the interproximal space opposite the tower and in the interior of the mouth; and utilizing the floss within the interproximal space;

wherein said providing step includes the further step of configuring the second support to include a means to prevent translation of said floss away from said second support and toward said tower, whereby used floss having passed beyond said supporting means of said second support is prevented from backing up into a region between the second support and the tower, and including the further step of holding the floss adjacent to the floss supporting tool without translation with respect thereto with a hand of the user at a location of the floss nearer to the support means of the tower than to the support means of the second support, whereby the floss is held taut between the support means of the tower and the support means of the second support for effective flossing.

15. The method of claim 14 including the further steps of:

removing the tower from between the arch-wire and the interproximal space, releasing the floss with the hand of the user, relocating the flossing tool to position the tower between the arch-wire and an interproximal space to be cleaned, allowing the floss to draw slack and feed fresh floss from the tower and into a region between the tower and the second support by impacting the floss residing between the tower and the second support against the interproximal space to be flossed, retrapping the floss adjacent to the floss supporting tool with the hand of the user, and pulling the floss through the unidirectional means in a direction away from the support means of the second support until the floss is taut between the tower and the second support, and flossing the interproximal space.

16. A flossing instrument for locating and supporting floss in interproximal spaces between teeth of a user, the user having an arch-wire proximate to, yet spaced from the teeth and interproximal spaces, the flossing instrument comprising in combination:

a handle adapted to be grasped by a hand of the user, an arm formed with and extending away from said handle, a first support, configured as a tower and extending from a surface of said arm, said tower dimensioned with a thickness not greater than a distance between the arch-wire and the interproximal space, said tower including means for slideably supporting the floss, and a second support spaced from said tower, said second support including means for slideably supporting the floss;

whereby floss can be inserted, utilized and removed from interproximal spaces blocked by the arch-wire;

wherein said second support includes a unidirectional floss translation means said unidirectional means allowing the floss to pass from said slideable support means of said tower toward said slideable support means of said second support, but preventing the floss from translating from said second support toward said tower;

wherein said slideable support means of said tower is an aperture in said tower sized to allow the floss to pass therethrough;

wherein said handle includes a cavity on an interior thereof supporting floss therein, said cavity including an aperture sized to allow said floss to pass therethrough, the floss routed to exit said cavity aperture and then extend to said aperture in said tower;

wherein said tower extends substantially perpendicularly from said arm;

wherein an arm aperture is provided between said cavity aperture and said tower aperture, said arm aperture passing from a top surface of the arm which supports said tower thereon through to a bottom surface of the arm opposite the top surface;

whereby the floss can pass through the arm to a side of the arm opposite the tower where the floss can be conveniently trapped by the hand of a user, thereby preventing unneeded floss from exiting said cavity during the flossing operation.

17. The flossing instrument of claim 16 wherein said unidirectional means is a plurality of prongs extending from bases thereof affixed to a backside of the second support distant from said tower, said prongs oriented in a crossed pattern with a crotch therebetween, said crotch dimensioned to frictionally receive the floss proximate thereto in a manner preventing the floss from translation toward said bases of said prongs, said bases of said prongs oriented closer to said slideable supporting means of said second support than distal ends of said prongs distant from said bases, said prongs including knobs thereon at said distal ends;

whereby the floss is allowed to pass beyond said knobs and into said crotch without severing thereof, but said knobs inhibit the floss from exiting said crotch.

18. The flossing instrument of claim 16 wherein said unidirectional means is a slit located on a backside of said second support distant from said tower, said slit having a first end closer to said slideable support means of said second support than a second end of said slit, said second end having a width greater than a width of the floss and said first end having a width not greater than the width of the floss;

whereby when the floss is threaded through said slit, the floss travels more easily from said first end to said second end than from said second end to said first end.

19. The flossing instrument of claim 16 wherein said unidirectional means is a series of teeth bounding sides of a groove, said teeth each having a surface distant from the slideable supporting means of said second support which is substantially perpendicular to said groove and surfaces of each tooth closest to the slideable supporting means having a nonperpendicular orientation with respect to said groove, whereby floss within said groove is more easily encouraged to pass through said groove away from said slideable supporting means than to pass through said groove toward said slideable supporting means.

20. The flossing instrument of claim 16 wherein said tower includes a base which is removably attachable to said top surface of said arm, whereby said tower can be replaced with other towers having different characteristics.

21. The flossing instrument of claim 20 wherein said tower includes filaments extending substantially perpendicularly away from said tower, said filaments configured to encourage plaque and other debris interposed between the arch-wire and the teeth of the user to be dislodged therefrom, whereby the tower not only supports the floss for flossing the interproximal spaces, but also cleans an area between the arch-wire and the teeth of the user.

22. A method for flossing interproximal spaces between teeth which have an arch-wire proximate thereto, but spaced therefrom, the steps including:

providing a flossing tool with a first support configured as a tower and dimensioned to fit between the arch-wire and the teeth of the user, the tower including a means to slideably support the floss thereon, and a second support with a means to slideably support the floss, the second support spaced from the tower a distance not less than a length of the interproximal spaces;

supporting floss between the support means of the tower and the support means of the second support;

locating the tower between the arch-wire and the interproximal space to be flossed;

locating the second support on a side of the interproximal space opposite the tower; and utilizing the floss within the interproximal space;

wherein said providing step includes the further step of configuring the second support to include a means to prevent translation of said floss away from said second support and toward said tower, whereby used floss having passed beyond said supporting means of said second support is prevented from backing up into a region between the second support and the tower;

including the further step of holding the floss adjacent to the floss supporting tool without translation with respect thereto with a hand of the user at a location of the floss nearer to the support means of the tower than to the support means of the second support, whereby the floss is held taut between the support means of the tower and the support means of the second support for effective flossing;

including the further steps of:

removing the tower from between the arch-wire and the interproximal space, releasing the floss with the hand of the user, relocating the flossing tool to position the tower between the arch-wire and an interproximal space to be cleaned, allowing the floss to draw slack and feed fresh floss from the tower and into a region between the tower and the second support by impacting the floss residing between the tower and the second support against the interproximal space to be flossed, retrapping the floss adjacent to the floss supporting tool with the hand of the user, and pulling the floss through the unidirectional means in a direction away from the support means of the second support until the floss is taut between the tower and the second support.

23. The method of claim 22 wherein said pulling the floss through the unidirectional means step includes holding the floss to prevent floss travel, whereby the unidirectional means is assisted in preventing floss travel from the second support to the tower.

24. A flossing instrument for locating and supporting floss in interproximal spaces between teeth of a user, the user having an arch-wire proximate to, yet spaced from the teeth and interproximal spaces, the flossing instrument comprising in combination:

a handle adapted to be grasped by a hand of the user, an arm formed with and extending away from said handle, a first support, configured as a tower and extending from a top surface of said arm, said tower dimensioned with a thickness not greater than a distance between the arch-wire and the interproximal space, said tower including an aperture therein for slideably supporting the floss, and a second support extending from said top surface of said arm, and spaced from said tower, said second support including means for slideably supporting the floss to be inserted, utilized and removed from interproximal spaces blocked by the arch-wire;

said handle includes a cavity on the interior thereof supporting floss therein, said cavity including an aperture sized to allow floss to pass therethrough, and an arm aperture between said cavity aperture and said tower aperture, said arm aperture passing through both a bottom surface of said arm and said top surface of said arm, the floss routed to exit said cavity aperture then pass through said arm aperture and then extend to and through said tower aperture;

whereby the floss on said bottom surface of said arm and between said cavity aperture and said arm aperture can be conveniently trapped by the hand of a user, thereby preventing unneeded floss from exiting said cavity during the flossing operation.

25. A method for flossing interproximal spaces between teeth which have an arch-wire proximate thereto, but spaced therefrom, the steps including:

providing a flossing tool with a first support configured as a tower and dimensioned to fit between the arch-wire and the teeth of the user, the tower including a means to slideably support the floss thereon, and a second support with a means to slideably support the floss, the second support spaced from the tower a distance not less than a length of the interproximal spaces;

supporting floss between the support means of the tower and the support means of the second support;

locating the tower between the arch-wire and the interproximal space to be flossed;

locating the second support on a side of the interproximal space opposite the tower, and holding the floss adjacent to said flossing tool without translation with respect thereto with a hand of the user at a location of the floss nearer to the support means of the tower than to the support means of the second support, whereby the floss is held taut between the support means of the tower and the support means of the second support for effective flossing;

utilizing the floss within the interproximal space;

removing the tower from between the arch-wire and the interproximal space;

releasing the floss with the hand of the user;

relocating the flossing tool to position the tower between the arch-wire and an interproximal space to be cleaned;

allowing the floss to draw slack and feed fresh floss from the tower and into a region between the tower and the second support by impacting the floss residing between the tower and the second support against the interproximal space to be flossed;

retrapping the floss adjacent to the floss supporting tool with the hand of the user, and pulling the floss through a unidirectional means in a direction away from the support means of the second support until the floss is taut between the tower and the second support, and flossing the interproximal space.

26. A flossing instrument for locating and supporting floss in interproximal spaces between teeth of a user, the user having an arch-wire proximate to, yet spaced from the teeth and interproximal spaces, the flossing instrument comprising in combination:

a handle adapted to be grasped by a hand of the user, said handle having a longitudinal axis, an arm having a proximal end connected to said handle and extending away from said handle and located on said longitudinal axis, a first support, configured as a tower and extending from a surface of said arm, at an intermediate location on said arm, said tower dimensioned with a thickness not greater than a distance between the arch-wire and the teeth of the user, said tower including a distal end spaced from said arm, said distal end having a closed surface, said tower including means for slideably supporting the floss, and a second support at a distal end of said arm remote from said handle and coplanar with said tower, said second support including means for slideably supporting the floss, said second support spaced from said tower by a distance not less than a length of the interproximal spaces;

said floss interposed between said tower and said second support.

27. The instrument of claim 26 wherein said second support and first support are parallel to each other and extend from said same surface of said arm, and wherein said tower of said first support is solid.

* * * * *